United States Patent [19]
Nelson

[11] Patent Number: 5,939,888
[45] Date of Patent: Aug. 17, 1999

[54] DIGITAL METHOD AND APPARATUS FOR MONITORING MOISTURE CONTENT

[75] Inventor: George F. Nelson, Coon Rapids, Minn.

[73] Assignee: New Holland North America, Inc., New Holland, Pa.

[21] Appl. No.: 08/917,421

[22] Filed: Aug. 26, 1997

[51] Int. Cl.[6] .................................................. G01N 22/04
[52] U.S. Cl. ........................ 324/640; 324/639; 324/641
[58] Field of Search ................... 324/616, 637, 324/639, 640, 641, 647; 73/73; 460/7

[56] References Cited

U.S. PATENT DOCUMENTS

| | | | |
|---|---|---|---|
| 3,693,079 | 9/1972 | Walker | 324/640 X |
| 4,764,718 | 8/1988 | Revus et al. | 324/640 |
| 5,708,366 | 1/1998 | Nelson | 324/640 |
| 5,716,272 | 2/1998 | Nelson | 460/7 |

OTHER PUBLICATIONS

Kraszewski, "Microwave Monitoring Moisture Content In Grain–Further Considerations"; International Microwave Power Institute, 1988; vol 23 No. 4, 1988; pp. 236–246. (Month unavailable).

Powell et al., "Use of a Density–Independent Function and Microwave Measurement System For Grain Moisture Measurement"; 1988 Am. Society of Agricultural Eng.; vol 31(6); pp. 1875–1881, Nov.–Dec., 1988.

King et al. "Microwave Moisture Measurement of Grains"; IEEE Transactions on Instrumentation and Measurement, vol. 41, No. 1, Feb. 1992; pp. 111–115.

McLendon et al., "Density–Independent Microwave Measurement of Moisture Content in Static and Flowing Grain"; 1993 Am. Society of Agricultural Engineers, vol. 36(3) May–Jun. 1993; pp. 827–835.

"Microwave Sensors for Process Control Part I: Transmission Sensors"; Ray J. King, KDC Technology Corp.; Sensors, Sep. 1992; pp. 68–74.

*Primary Examiner*—Glenn W. Brown
*Attorney, Agent, or Firm*—Griffin, Butler, Whisenhunt & Szipl, LLP

[57] ABSTRACT

A monitor for monitoring the moisture content of grain comprises at least one programmable PIN diode attenuator connected between a microwave measurement signal source and a transmit antenna. A controller stores an addressable attenuation table, each location in the table storing an attenuation value and an associated attenuator address. A counter accesses the table locations sequentially and the attenuator addresses are applied to the attenuator to cause a step-wise decreasing attenuation of the measurement signal which is then transmitted through the grain. After the signal passes through the grain, it is detected and applied to a threshold comparator. When the magnitude of the detected signal reaches the threshold, the counter is stopped and the attenuation value at the location pointed to by the counter is taken as the attenuation of the measurement due to moisture in the grain. Once the attenuation has been determined, the moisture content and mass grain flow may be calculated. The determination of attenuation and moisture content is accomplished with digital circuitry and the determination of attenuation requires only a go no-go comparison of the measurement signal with a threshold value.

13 Claims, 1 Drawing Sheet

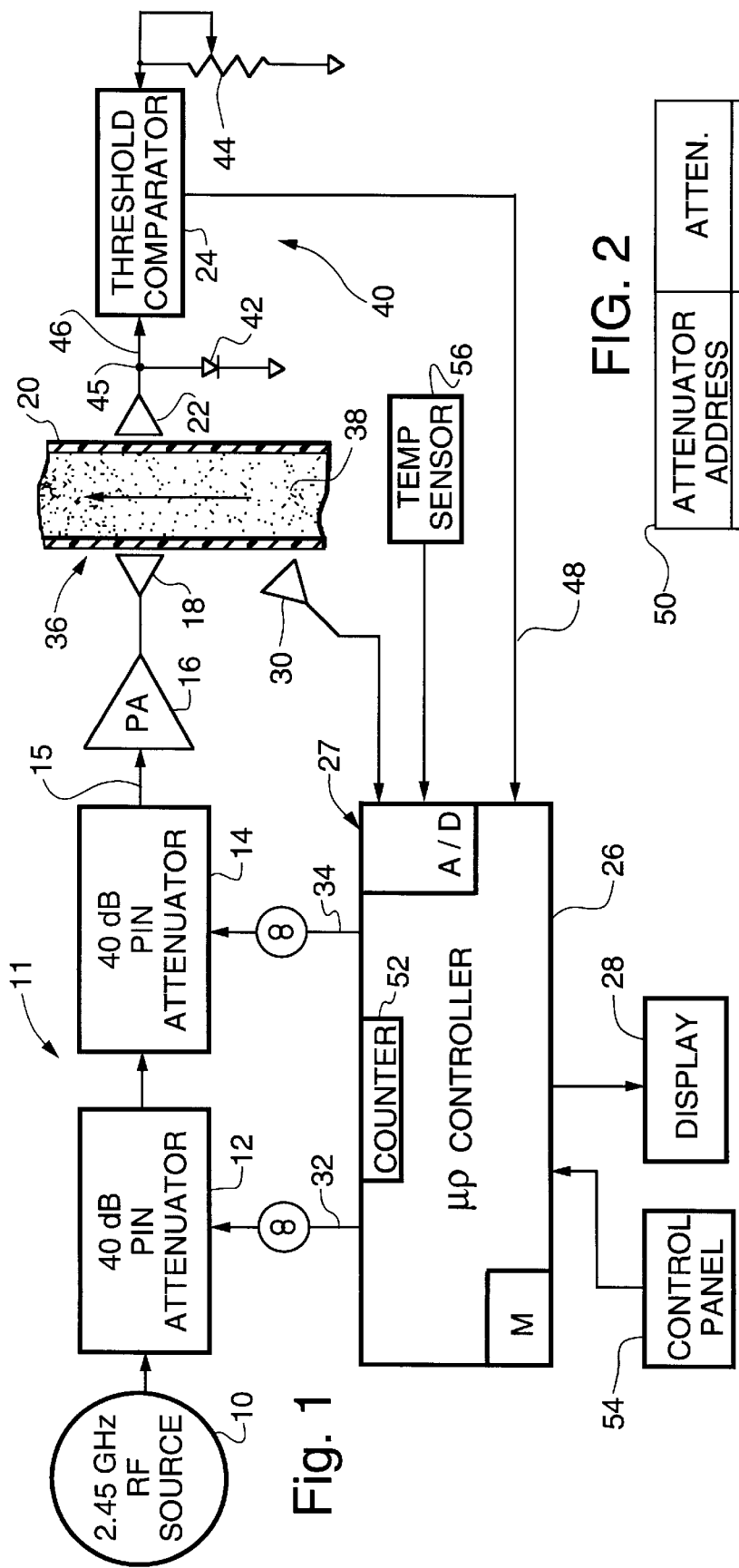

DIGITAL METHOD AND APPARATUS FOR MONITORING MOISTURE CONTENT

RELATED APPLICATIONS

This application incorporates by reference the disclosure of concurrently filed application Ser. No. 08/917,481, now U.S. Pat. No. 5,871,397 of Nelson et al. entitled Improved Grain Monitor, assigned to the same assignee as this application.

FIELD OF THE INVENTION

The present invention relates to microwave grain monitors of a type suitable for use on agricultural grain harvesters to measure grain moisture content and crop yield as the grain is harvested. More particularly, the invention relates to a novel method and apparatus for determining the moisture content of a flowing material such as grain by attenuating, in discrete steps, the power of a measurement signal applied to a transmit antenna disposed on one side of a sample region through which the material flows and detecting when the power at a receiving antenna, disposed on the opposite side of the sample region, crosses a threshold level.

BACKGROUND OF THE INVENTION

Microwave grain monitors employing analog circuits for determining crop yield and the moisture content of grain are well known in the art. Typically, the prior art systems comprise an RF frequency source for applying a constant power microwave measurement signal in the range of 1 to 10 GHz to a transmit antenna disposed on one side of a sample region containing a grain sample, a receive antenna disposed on the opposite side of the sample region, analog circuits connected to the receive antenna and the signal source for producing indications of the phase shift and attenuation imposed on the measurement signal during its passage through the grain sample, and a computer responsive to the indications of the attenuation and phase shift for determining the moisture content and bulk grain density of the grain. Once the moisture content and bulk density have been determined, crop yield may be determined from these values and from a measurement of grain mass flow through the sample region, the flow measurement typically being made by a Doppler microwave transceiver. A typical microwave system for measuring the moisture content of grain is described by King et al. in a technical paper entitled Microwave Moisture Measurement of Grains, published in the IEEE Transactions on Instrumentation and Measurement, Vol. 41, No.1, February 1992, pp. 111–115.

Prior art systems employ analog receiver circuits including expensive linear receiver amplifiers, detectors and baseband amplifiers to detect the phase shift and attenuation imparted to the measurement signal as it passes through a grain sample. Such systems require a fixed RF power from the transmitter sufficient to overcome all losses and still produce a good signal output. The receiver must be linear from the noise floor to maximum input power so that it will not distort the test results. The dynamic ranges of the prior systems have had to include no signal input to maximum transmit input signals resulting in a dynamic range of from 60 to 80 dB.

Most prior art systems measure both the attenuation and the phase shift imparted to a measurement signal in passing through the grain, and moisture content is computed from these values using an experimentally developed formula. The above-referenced copending application discloses an improved grain monitor wherein moisture content is determined by measuring only the attenuation. Phase shift is primarily a function of bulk grain density whereas attenuation is primarily a function of moisture content. The referenced application teaches that, by maintaining a substantially constant bulk grain density in the sampling region, moisture content may be determined by measuring the attenuation only, and with only slightly less accuracy (1.2% error versus 1.0% error) than when both phase shift and attenuation are measured. While this system represents an improvement over the prior art in that it avoids the use of the circuits for determining phase shift, it still employs relatively expensive linear analog receiver circuits for measuring the attenuation.

SUMMARY OF THE INVENTION

An object of the present invention is to provide a method and apparatus for determining moisture content of a sample using digital techniques, thus avoiding the use of expensive linear analog circuits.

Another object of the invention is to provide a moisture monitor wherein the receiver circuits for processing the measurement signal after its passage through a sample have no analog components and no requirements for dynamic range.

A further object of the invention is to provide a method and apparatus for determining the moisture content of a sample without directly measuring the attenuation of the measurement signal as it passes through the sample. To accomplish this, an attenuation table is established in a memory device. Each location in the table includes an attenuator address and a corresponding attenuation value. An RF measurement signal of fixed magnitude is applied to a calibrated programmable attenuator. The attenuator addresses are successively read out of the table and applied to the attenuator which attenuates the measurement signal in successive discrete steps, the degree of attenuation at each step being precisely known. The measurement signal, the power of which now varies in a step-wise manner, is applied to a transmit antenna disposed on one side of a sample region. Grain is pushed upwardly in a tube which extends through the sample region. A receive antenna detects the measurement signal after it passes through the sample region and is further attenuated by moisture in a sample flowing through the sample region. The receive antenna is connected to a threshold comparator which compares the magnitude of the received measurement signal with a threshold value. When the received measurement signal exceeds the threshold value, the progressive attenuation of the measurement signal is stopped and the attenuation value corresponding to the attenuator address which caused the threshold to be exceeded is read out of the table as the attenuation due to moisture in the sample. Once the attenuation due to moisture has been determined, the moisture content is calculated using a table of grain coefficients, the table of coefficients being stored in a memory and containing a set of grain coefficients for each type of grain which may be harvested.

Yet another object of the invention is to provide a method of determining the attenuation of an RF measurement signal by the moisture content of a sample without direct measurement of the attenuation of the signal in passing through the sample, that is, without comparing the magnitudes of the measurement signal before and after it has passed through the sample. According to this method, a microwave measurement signal of fixed power is successively attenuated in known steps so as to provide a measurement signal which increases in discrete steps. The measurement signal is transmitted through the sample, detected, and compared to a threshold value. When the detected signal exceeds the threshold, the stepping of the attenuation is stopped and an attenuation value is read from a stored table as an indication of the attenuation of the measurement signal by the sample. The table contains a location corresponding to each attenuation step. The attenuation values are chosen such that if the microwave were subjected to an attenuation equal to the sum of the corresponding attenuation step and the attenuation represented by the attenuation value, the signal would have a magnitude equal to the threshold.

Other objects and advantages of the invention will become apparent upon consideration of the following description and the accompanying drawings.

BRIEF DESCRIPTION OF THE DRAWINGS

FIG. 1 is a schematic block diagram of the grain monitor showing transmit and receive antennas disposed on opposite sides of a sample region in a harvesting machine; and, FIG. 2 illustrates an attenuation table.

DESCRIPTION OF PREFERRED EMBODIMENT

As illustrated in FIG. 1, a grain monitor according to the present invention comprises an RF signal source 10, an attenuator means 11 comprising first and second attenuators 12 and 14, a power amplifier 16, a transmit antenna 18, a sample container 20, a receive antenna 22, an RF power detector diode 42, a threshold comparator 24, a microprocessor controller 26 and a display 28.

Signal source 10 is an RF microwave signal source producing a microwave measurement signal of fixed power and having a frequency greater than about 1 GHz, preferably about 2.45 GHz.

The microwave signal produced by signal source 10 is applied to the input of the first attenuator 12 and the output of attenuator 12 is connected to the input of the second attenuator 14. Attenuators 12 and 14 are precisely calibrated programmable attenuators and preferably comprise programmable PIN diode attenuators such as the model AGH-2040DD sold commercially by American Microwave Corp.

Attenuators 12 and 14 are controlled by 12 bits of 16-bit attenuator address signals applied thereto by controller 26. Eight of the address bits are applied via bus 32 to attenuator 12 and the other eight bits are applied to attenuator 14 via bus 34 but in the embodiment described herein only six of each eight bits are used to program an attenuator. Each address applied to one of the attenuators causes the attenuator to introduce a particular level of attenuation into the signal being received at its input. Thus, the attenuators 12 and 14 together may be programmed by the address signals so as to attenuate the microwave signal from source 10 by 0 to 80 dB in 4096 ($2^{12}$) increments or discrete steps of approximately 0.02 dB. In a preferred embodiment, the controller controls the attenuators to decrease the attenuation in steps so that the measurement signal appearing at the output 15 of attenuator 14 has a known power level which increases in sequential discrete steps.

It will be understood that, depending on the degree of accuracy desired and the characteristics of available attenuators, one attenuator may suffice or more than two attenuators may be required. Also, it is not necessary to use all of the possible attenuation levels. Furthermore, as will be evident from the following description, the attenuators may be programmed to increase the attenuation in steps rather than decrease it.

The measurement signal appearing at the output of attenuator 14 is applied through amplifier 16 to the transmit antenna 18. Amplifier 16 may be a conventional linear RF power amplifier.

Transmit antenna 18 and receive antenna 22 are preferably custom designed printed circuit patch antennas. Such antennas are described in "MicroStrip Antennas" by I. J. Bahl, P. Bhartia. Conventional horn antennas may be used but printed circuit patch antennas permit installation in very small regions where sensor size is a consideration.

Antennas 18 and 22 are disposed on opposite sides of a sensor region 36. As illustrated in FIG. 1, container 20 is a feed tube of a grain harvester. Grain 38 is pushed upwardly through the tube by a conventional auger (not shown) in order to obtain a uniform density of the grain in the sensor region between antennas 18 and 22. The container 20 is made of a plastic or other material, or has a window made of such material, which is transparent to microwaves passing through the sensor region.

Transmit antenna 18 transmits the attenuated measurement signal toward receive antenna 22 and as the signal passes through the sensor region 36 it is further attenuated by moisture in the grain 38 passing through the sensor region. The attenuated measurement signal received at antenna 22 is applied to a threshold comparator means 40 comprising the threshold comparator 24, the RF power detector diode 42 and a potentiometer or variable resistance 44.

Detector diode 42 is connected to a bias voltage (shown as ground) at one side and at the other side it is connected to a junction 45 between the receive antenna 22 and the input 46 of the threshold comparator 24. The detector diode 42 rectifies the measurement signal received at receive antenna 22 so that a rectified voltage, proportional to the power of the received signal, is applied to the input of the threshold comparator.

The potentiometer 44 is for calibration purposes. Calibration is carried out with no grain in the sample region. The attenuators 12 and 14 are programmed for minimum (zero) attenuation of the signal produced by source 10 and the potentiometer is adjusted to the point where the threshold comparator produces an output signal on lead 48.

The microprocessor controller 26 is conventional in that it includes a programmable microprocessor, an analog to digital converter 27 with multiplexed inputs, and a memory M comprising RAM, ROM and Flash EEPROM memory sections. In accordance with the present invention, an attenuation table 50 (FIG. 2) is provided in a non-volatile portion of memory M. As illustrated in FIG. 2, the attenuation table comprises a plurality of addressable locations, each location storing an attenuation value (attend.) and an associated 12-bit attenuator address.

An attenuation measurement cycle is started by a timed interrupt initiated by a timer (not shown) in the microprocessor. When the measurement cycle is started, a counter 52, implemented within the microprocessor, begins sequentially addressing the locations in table 50 and the attenuator addresses therein are read out and applied to attenuators 12 and 14. This causes the attenuators to attenuate the measurement signal, the attenuation decreasing in discrete steps as successive attenuator addresses are applied.

As the attenuation decreases, the power of the measurement signal transmitted by antenna 18 increases. The signal is further attenuated by moisture as it passes through the grain in sensor region 36 to the receive antenna but still appears at detector diode 42 as a microwave signal which periodically increases in magnitude. After rectification by diode 42, the resulting voltage signal is applied to the threshold comparator 24. When the voltage exceeds the threshold voltage of the comparator, the comparator produces an output pulse on lead 48 to interrupt the microprocessor. This stops the incrementing of counter 52. The contents of the stopped counter may be used to again address the same location to read from table 50 the attenuation value corresponding to the attenuation address which caused the threshold to be exceeded. Obviously, an attenuation value in table 50 could be read out at the same time that its corresponding attenuation address is read, the attenuation value being discarded if the attenuation address does not cause the threshold to be exceeded. In either event, the attenuation value read from table 50 indicates the attenuation of the measurement signal caused by moisture in the grain in the sensor region 36. This attenuation value is saved in a register for subsequent use in computing the moisture content.

The attenuation values stored in table 50 are determined as follows. The total attenuation, in decibels, necessary to reduce the power of the output signal from source 10 to the threshold level at which the threshold comparator 24 produces an output pulse is:

$$dB = 10 \log P_1/P_2$$

where $P_1$ is the power of the signal from source 10 and $P_2$ is the power at diode 42 necessary to trigger the comparator output. The total attenuation is made up of the known programmed attenuation, introduced by attenuators 12 and 14, and the unknown attenuation caused by the moisture content of the sample in sensor region 36. Each attenuation value in table 50 is selected such that if the sample region is empty and an attenuation as represented by the attenuation value is inserted (theoretically) in the measurement signal path together with its corresponding programmed attenuation, the signal from source 10 will be reduced to the threshold level.

After an attenuation measurement cycle has been completed to determine the attenuation, grain moisture content and grain mass flow may be determined as described in the aforementioned copending application. Grain density is a factor in the calculation of moisture content and the grain density, in turn, is dependent on the temperature of the grain. Therefore, a temperature sensor 56 is provided for sensing the temperature of the grain in, or near, the sensor region 36. The temperature sensor produces an output voltage proportional to the grain temperature and this voltage is periodically sampled and digitized by A/D converter 27 and saved.

Grain mass flow requires a measurement of the rate of grain flow through the sensor region 36. A conventional Doppler transceiver 30 senses the velocity of the grain flowing through tube 20. The transceiver output signal is periodically sampled and digitized by A/D converter 27 and saved.

As taught in the referenced copending application, grain moisture content is determined utilizing a table of grain coefficient values. The table is stored in the Flash EEPROM portion of memory M and contains sets of experimentally determined grain coefficients, one set for each type of grain (red wheat, winter wheat, corn soybeans, etc.) to be harvested. The sets of coefficients are entered into the memory via keys or pushbuttons located on an operator's control panel 54. Prior to the start of a harvesting session, the harvester operator enters into the microprocessor, via control panel 54, an indication of the type of grain which is to be harvested. This indication is used to select the appropriate set of coefficients for the calculation of moisture content.

The moisture content is calculated by microprocessor 26 by first reading from the Flash EEPROM section of memory M the set of grain coefficients for the type of grain being harvested. The set of grain coefficients comprises wet grain coefficients $\alpha_w$, $\beta_w$, $\gamma_w$, $\delta_w$ and $T_{0w}$, and dry grain coefficients $\alpha_d$, $\beta_d$, $\gamma_d$, $\delta_d$ and $T_{0d}$, where $T_{0w}$ is the temperature at which the other wet grain coefficients were experimentally determined and $T_{0d}$ is the temperature at which the other dry grain coefficients were experimentally determined.

Since the packing density of the grain moving through the sensor region 36 is influenced by the grain temperature, wet and dry temperature compensation factors are computed according to the equations:

$$Tcomp_w = \gamma_w (\delta_w{}^{log(T_{0w}-T)}) \text{ if } T > T_{0w}$$

$$Tcomp_w = 0 \text{ if } T < T_{0w}$$

$$Tcomp_d = \gamma_d (\delta_d{}^{log(T_{0d}-T)}) \text{ if } T > T_{0d}$$

$$Tcomp_d = 0 \text{ if } T < T_{0d}$$

where T is the temperature of the flowing grain as sensed by sensor 56.

Next, the microprocessor computes the wet density ($D_w$) and the dry density ($D_d$) via the formulas $$D_w = \alpha_w + \beta_w \log(atten) + Tcomp_w$$

$$D_d = \alpha_d + \beta_d \log(atten) + Tcomp_d$$

where (atten) is the attenuation value read from table 50 as described above.

The total density $D_t$ is then determined by adding the wet and dry densities $D_w$ and $D_d$. Finally, the moisture content is calculated by the formula:

$$MC = D_w/D_t.$$

After the moisture content has been calculated, it is saved in a register or memory location so that it may be called up for display on the display 28 when the operator actuates the appropriate keys on the control panel 54.

The yield or grain mass flow is calculated by first determining the volume flow in a conventional manner. The output of the Doppler velocity sensor 30 is digitized, the frequency shift determined, and the grain velocity determined from the phase shift. The velocity is then multiplied by a constant stored in memory M and representing the cross sectional area of the tube 20. After appropriate units conversion, such as kg/min, the resulting volume flow is multiplied by the density to obtain the mass flow.

Both the volume flow and mass flow are saved for display on the display 28 as commanded by operator selection from the control panel 54.

Although the invention was developed for specific use in the measurement of grain moisture content as the grain is being harvested, and has been described in that environment, the principles of the invention are equally applicable to the measurement of the moisture content of other materials. The materials do not have to be moving through the sample region but may be stationary therein, and need not be confined in a container so long as a constant density is maintained. Furthermore, obvious modifications may be made in the described embodiment without departing from the spirit and scope of the invention as defined by the appended claims. For example, the attenuator means 11 may be sequenced so as to decrease the power of the transmitted measurement signal in discrete steps, rather than increase it. In this case the threshold comparator 24 is chosen so as to produce an output pulse on lead 48 when the magnitude of the measurement signal received at antenna 22 crosses or exceeds the threshold in the negative direction. The invention is not limited to the disclosed algorithm for determining moisture content and density and other algorithms may be used.

I claim:

1. A method of determining the attenuation of a measurement signal by a sample in a sample region, said method comprising:

(a) generating a fixed power microwave signal;

(b) subjecting said microwave signal to a known programmed attenuation which varies in discrete steps to produce a measurement signal having a power which varies in discrete steps;

(c) establishing a plurality of attenuation values, each attenuation value being associated with a corresponding step of said known programmed attenuation;

(d) transmitting said measurement signal along a measurement signal path through a sample in said sample region and detecting when the power of the measurement signal, after passage through said sample region, reaches a threshold level; and (e) when the detected measurement signal reaches said threshold level, selecting, as the attenuation of the measurement signal by the sample, the attenuation value associated with the step of said known programmed attenuation which caused the detected measurement signal to reach said threshold level, (f) the plurality of attenuation values being established by selecting values such that if the sample region were empty and an attenuation represented by a given attenuation value were inserted into the measurement signal path together with its corresponding known programmed attenuation, the microwave signal would reach said threshold level.

2. A method as claimed in claim 1 wherein step (b) is terminated when the detected measurement signal reaches said threshold level.

3. A method as claimed in claim 1 wherein step (b) comprises subjecting the microwave signal to a known programmed attenuation which decreases in discrete steps so that the power of said measurement signal increases in discrete steps.

4. A method as claimed in claim 3 wherein step (d) comprises detecting when the power of the measurement signal exceeds said threshold level.

5. A method as claimed in claim 1 wherein step (b) comprises subjecting the microwave signal to a known programmed attenuation which increases in discrete steps so that the power of said measurement signal decreases in discrete steps.

6. A monitor having digital means for determining the attenuation of a measurement signal by a sample, said monitor comprising:

measurement signal generating means for generating a measurement signal having a power level which varies in discrete steps;

a memory for storing an attenuation table holding attenuation values, each attenuation value being associated with a respective one of the power level steps;

a transmit antenna for transmitting the measurement signal through the sample;

a receive antenna for receiving the transmitted measurement signal after said measurement signal has passed through the sample;

detector means connected to said receive antenna for detecting when the power of the measurement signal, after passage through the sample, reaches a threshold level; and, means responsive to said detector means when the detected measurement signal reaches said threshold level for selecting from the attenuation table, as the attenuation of said measurement signal by the sample, the attenuation value associated with the power level of said measurement signal which caused the detected measurement signal to reach said threshold level.

7. A monitor as claimed in claim 6 wherein said measurement signal generating means comprises:

an RF signal source producing a microwave signal at a fixed power level;

programmable attenuator means for selectively attenuating said microwave signal in discrete digital steps so as to produce as said measurement signal a signal which increases in magnitude by discrete steps; and, a digital controller for applying signals to said programmable attenuator means to select the attenuation of said microwave signal by said programmable attenuator means.

8. A monitor as claimed in claim 7 wherein said programmable attenuator means comprises at least one PIN diode attenuator.

9. A monitor as claimed in claim 7 wherein said programmable attenuator means comprises a plurality of PIN diode attenuators.

10. A monitor as claimed in claim 7 wherein said attenuation table has a plurality of addressable locations, each of said locations storing one of said attenuation values and an attenuator address for addressing said programmable attenuator means, said digital controller including means for addressing said locations to sequentially apply the attenuator addresses to said programmable attenuator means to thereby control the attenuation of said microwave signal.

11. A monitor as claimed in claim 10 wherein said detector means comprises a voltage comparator for comparing an input voltage with a reference voltage level, and an RF diode detector connected between said receive antenna and said voltage comparator, said diode detector rectifying the measurement signal received at said receive antenna to provide said input voltage to said voltage comparator, said voltage comparator producing an output pulse when the input voltage reaches the reference voltage level, said digital controller being responsive to said output pulse to stop the addressing of said attenuation table when the input voltage reaches the reference voltage level.

12. A monitor as claimed in claim 6 wherein said transmit antenna and receive antenna each comprise a printed circuit patch antenna.

13. A monitor as claimed in claim 6 and further comprising a temperature sensor for sensing ambient temperature, a memory for storing a set of grain coefficients, and microprocessor means responsive to said temperature sensor for calculating the moisture content of grain from the sensed temperature, the set of grain coefficients, and the attenuation value selected from said attenuation table.

* * * * *